United States Patent [19]

Yang

[11] Patent Number: 5,811,262
[45] Date of Patent: Sep. 22, 1998

[54] HEPATOCELLULAR CARCINOMA ONCOGENE

[75] Inventor: Stringer S. Yang, Bethesda, Md.

[73] Assignee: The United States of America as represented by the Secretary of the Department of Health and Human Services, Washington, D.C.

[21] Appl. No.: 324,445

[22] Filed: Oct. 18, 1994

Related U.S. Application Data

[63] Continuation of Ser. No. 575,524, Aug. 31, 1990, abandoned, which is a continuation-in-part of Ser. No. 451,953, Dec. 19, 1989, abandoned.

[51] Int. Cl.⁶ .......................... C12P 21/02; C07K 14/435
[52] U.S. Cl. ........................................... 435/69.1; 530/350
[58] Field of Search ................................. 530/350, 403; 435/69.1

[56] References Cited

U.S. PATENT DOCUMENTS 4,431,739  2/1984  Riggs ...................................... 435/69.1

OTHER PUBLICATIONS

Yang et al. Leukemia vol. 2, No. 12 suppl. pp. 1025–1135 Dec. 1988.

*Primary Examiner*—George C. Elliott
*Attorney, Agent, or Firm*—Susan S. Rucker

[57] ABSTRACT

The present invention relates to an oncoprotein specific for hepatocellular carcinomas and to a nucleotide sequence that codes for such a protein. The invention further relates to screening and diagnostic methodologies (and kits based thereon) that make use of the oncoprotein (or antibodies specific for same) and the nucleotide sequence.

3 Claims, 9 Drawing Sheets

FIG. 1A

```
                                                       27                                      *   54                                              81
AAG CTT AAT AGA AAA TAT GAG CAA CAT ACA CAA ACA TTA GCA ACA ATG ATA TAA AAT ACC ACT TAA ACA TAA GGA AAA ATG
                                                                                                          MET
                                                                                                          162
TTG CCC TTC ACT TGT GGA AGA AAT GCA AAT GAA AAC AGC CCT AGG GAT GTT GAC GTT GGG GTG GCA CCT GCT GCA GAG GGT
Leu Pro Phe Thr Cys Gly Arg Asn Ala Asn Glu Asn Ser Pro Arg Asp Val Asp Val Gly Val Ala Pro Ala Ala Glu Gly
                                                                                                          243
AAC GTG CAG CAT GTC GAG GGC AGC GAG ACT GCC AAG GCT GGT TTG AGC TCA AGG TCA GGT GGA GGA GGT AGT CTC TCC CAT CTC
Asn Val Gln His Val Glu Gly Ser Glu Thr Ala Lys Ala Gly Leu Ser Ser Arg Ser Gly Gly Gly Gly Ser Leu Ser His Leu
                                                                                                          324
TTC TGC GAG TGC AGC TCT AAA CCC TGC CTG AAA CAC GTG GAG AAG CTA TCT GAG GAG CTG CCT CCA GGA CAC ATG CAA ATG GAC
Phe Cys Glu Cys Ser Ser Lys Pro Cys Leu Lys His Val Glu Lys Leu Ser Glu Glu Leu Pro Pro Gly His MET Gln MET Asp
                                                                                                          405
ACT CTG ATC ATA AAA TTA TCA GGA AGA TTG AGA AAT AAG ACA AAA ATG GAG GTG CCA CCA AAC CAG TGG AAA TTT TTC CCC
Thr Leu Ile Ile Lys Leu Ser Gly Arg Leu Arg Asn Lys Thr Lys MET Glu Val Pro Pro Asn Gln Trp Lys Phe Phe Pro
                                                                                                          486
TTT TCA TTC CTC TGG CAT TCC CTG ACT CAA GGC AGC CCA CAC TCT AGG AGC AGA CAC CAG GGC ACA GGT GGG GAG
Phe Ser Phe Leu Trp His Ser Leu Thr Gln Gly Ser Pro His Ser Arg Ser Arg His Gln Gly Thr Gly Gly Glu
                                                                                                          567
CTC TGG GGG ACC CTC CAG GCT TAC TCA GTG AAT GGG TTA GCA GCA GCC ACC ATG GAG GCC CCT GCA GGG ACC CAC
Leu Trp Gly Thr Leu Gln Ala Tyr Ser Val Asn Gly Leu Ala Ala Ala Thr MET Glu Ala Pro Ala Gly Thr His
                                                                                                          648
AAC ACT GAG AGG GAT CTT GCC TCT AAT CAG ATA AGC TGT GAT TCC CGA GAG GGT GGG GTA AAG GCC ACG GGT CTT TTT
Asn Thr Glu Arg Asp Leu Ala Ser Asn Gln Ile Ser Cys Asp Ser Arg Glu Gly Gly Val Lys Ala Thr Gly Leu Phe
                                                                                                          729
CTC TCC ACA TCT TCC CAC GTC ATG TGT GAG CAC CGT GAC TGT AAG AGA GGG CGA AGA AAG GGT GGA CAC ATA ATG AGC CGC AGC
Leu Ser Thr Ser Ser His Val MET Thr Pro Glu Gly Arg Arg Arg Gly Arg Arg Lys Cys Glu His Arg Asp Ile MET Ser Arg Ser
```

FIG. 1B

```
     756                    783                       810
CTT CTG ACT AGA TGC CCC AAA GAA TCC CAG ACA CAG CAT CAG ACC AGA AAC TGC AGG GTA ATG AGG AAC TTT GGA
Leu Leu Thr Arg Cys Pro Lys Glu Ser Gln Thr Gln His Gln Thr Arg Asn Cys Arg Val MET Arg Asn Phe Gly
     837                    864                       891
AAG CAA TCC ATC GTG TTG TCA GTA AAA CCT CTG GCT CTG CAC CGA TCC CGA GCT GGG CAT GCA TGG ATG GTG ACC CTC GAT GGA ATA
Lys Gln Ser Ile Val Leu Ser Val Lys Pro Leu Ala His Arg Ser Arg Ala Gly His Ala Trp MET Val Thr Leu Asp GLY Ile
     918                    947                       974
GAC TAT GAG GAA CCA GGT GAG ATC TAC CTC CAC CGA GAC GTG AGA GTG ACC TGC ATA CCC AAA CAC CAT GAG GCT TTA
Asp Tyr Glu Glu Pro Gly Glu Ile Tyr Leu His Arg Asp Val Arg Val Thr Cys Ile Pro Lys His His Glu Ala Leu
     999                    1028                      1053
AAG ACT GAG CTG ATG TGG CCA CAG CCT CTG CAG GTT GCT CTG CAC CAT AAG CCC AAC CAC ATC AAT TGC TGC
Lys Thr Glu Leu MET Trp Pro Gln Pro Leu Gln Val Ala Leu His His Lys Pro Asn His Ile Asn Cys Cys
     1080                   1107                      1134
AAA ACA AAA CTA CAG CAT TCT CCA TAC CAC TTA AAT AAG ACA CTC ACA TTC AAA ACG CCC AGG ACA TCC
Lys Thr Lys Leu Gln His Ser Pro Tyr His Leu Asn Lys Thr Leu Thr Phe Lys Thr Pro Arg Thr Ser
     1161                   1188                      1215
AAA ATT ACT TCT ACA AAA AAT CAG GAA AAT CTC AAT GAG CAA GGA AAA TGG CAA TCA GTA GCT GCC AGT GCT GCT GAG ATG ACA
Lys Ile Thr Ser Thr Lys Asn Gln Glu Asn Leu Asn Glu Gln Gly Lys Trp Gln Ser Val Ala Ser Ala Glu MET Thr
     1242                   1269                      1296
ATG AGG GTT GGA ATC ATC AAC ATC TTT AAA GTA ATT CTC CAG CAA GTA ATG CAA AAC ACT CTT GAG ATA
MET Arg Val Gly Ile Ile Asn Ile Phe Lys Val Ile Leu Gln Gln Val MET Ala Asn Thr Leu Glu Ile
     1323                   1350                      1377
AAT GGA ATA AGA AGG CTC AGG GAG AAA GTG GAA TGT ACA AAG AAT GAC CAA GTG GGA ATT GCA CCA CTG GAA ACA AAT
Asn Gly Ile Arg Arg Leu Arg Glu Lys Val Glu Cys Thr Lys Asn Asp Gln Val Gly Ile Ala Pro Leu Glu Thr Asn
     1404                   1431                      1458
CAC CAG GAT AAA GCA GTC TCT GGC TGG GCC AAC AGG AGA ATG AAA AGG GAA ATG AAA AGG AGA GAA GTT ATG GCA GTT GTC CAA
His Gln Asp Lys Ala Val Ser Gly Trp Ala Asn Arg Arg MET Glu MET Lys Arg Arg Glu Val Met Ala Val Val Gln
```

FIG. 1C

```
                                              1485                              1512
                                               ↑                                 *
TTT GAA CAA CAC AAA AGA CAC TGA TTT AAA AAA TGA GGC AGG GCT CAG TGG CTC ACA CCT ATA ATC CCA ATA CCT TGG    1539
Phe Glu Gln His Lys Arg His

1566
            ↑
GAG GCC GAG GCA ATG TAT CAC CTG AGG TCA GGA GTT CAA GAC TAC CCT GGC CAA ATC CCA CAT GGC AAA TCT CTA CTG AAA    1620
                MET Tyr His Leu Arg Ser Gly Val Gln Asp Tyr Pro Gly Gln Ile Pro His Gly Lys Ser Leu Leu Lys

1647
ATA CAA GAA TTA GCT GGG CAT GGT GGC AGG TGC CTG CAA TCC CAG CTA CTC AGG AGG CAG GAG AAT CAC TTG AAC    1701
Ile Gln Glu Leu Ala Gly His Gly Gly Arg Cys Leu Gln Ser Gln Leu Leu Arg Arg Gln Glu Asn His Leu Asn

1728
TCG GGA GGT AGA GGG TGC AGT GAG CCA AAA TCG CAC CTC TGC ATT CCA GCC TGG GTG ACA GAG GGA GAC TCT GTC TCA AAA    1782
Ser Gly Gly Arg Gly Cys Ser Glu Pro Lys Ser His Leu Cys Ile Pro Ala Trp Val Thr Glu Gly Asp Ser Val Ser Lys

1809
CAA AAC ACA AAA AAT GAA CAG CAC CTC AGG AAC AAC AAT ACC AAA AAG TCC AAC AGC TGT ATA ATT GGT GGC CCA GAA GGA    1863
Gln Asn Thr Lys Asn Glu Gln His Leu Arg Asn Asn Thr Lys Lys Ser Asn Ser Cys Ile Ile Gly Gly Pro Glu Gly

1890
GAG GAG AAA GAG TGG AGT ACA GAA ATG AGA GAA ATG ACT GAT AAT GTT TCA ATT TTG AAA AAG GAC ATA AAC    1944
Glu Glu Lys Glu Trp Ser Thr Glu MET Arg Glu MET Thr Asp Asn Val Ser Ile Leu Lys Lys Asp Ile Asn

1971
CTA AAG ATT ATA GAT TCA AAA GCC CAG CTG AAT GCA GAT ATA AAT ACA GAT TTA TCA TTA AAC TGT GAA    2025
Leu Lys Ile Ile Asp Ser Lys Ala Gln Leu Asn Ala Asp Ile Asn Thr Asp Leu Ser Leu Asn Cys Glu

2052
ATA AAT TGG TTT TGT CAC CCA GCA TTG TCA CTG TGG GAG AAA AGA GAT CAA AAG TAC ACA AAG GAA GGA AAT ACA    2106
Ile Asn Trp Phe Cys His Pro Ala Leu Ser Leu Trp Glu Lys Arg Asp Gln Lys Tyr Thr Lys Glu Gly Asn Thr

2133
                                        ↓
GAA TAT TAT GGC CAT GGG AAA GAG GTG TCA GTG TGA ATA CAT AGA ACA CAC TTA AGC ACC AAC AAC CCC AAA TGA TGG GGC    2187
Glu Tyr Tyr Gly His Gly Lys Glu Val Ser Val •  Ile His Arg Thr Ala His Leu Ser Asn Asn Pro Lys • Trp Gly
```

HEPATOCELLULAR CARCINOMA ONCOGENE

This application is a continuation of application Ser. No. 07/575,524, filed Aug. 31, 1990, now abandoned, which is a Continuation-in-Part of application Ser. No. 07/451,953, filed Dec. 19, 1989, now abandoned.

BACKGROUND OF THE INVENTION

1. Technical Field

The present invention relates, in general, to a protein of hepatoma cells, and, in particular, to an oncoprotein that is an amplified gene expression product of hepatoma cells. The invention further relates to a nucleotide fragment coding for the oncoprotein, to a recombinant molecule that includes such a fragment and to cells transformed therewith. The invention further relates to methods of detecting the presence of hepatocellular carcinomas in a patient and to kits based thereon.

2. Background Information

Epidemiological evidence has led to a strong etiological implication of several DNA viruses with the occurrence of certain cancers and other disorders in humans. These include the papillomavirus in cervical carcinoma (HPV 16) and in epidermodysplasia verruciformis (HPV 3 and 8); the Epstein-Barr virus in Burkitt's lymphoma; and the hepatitis B virus (HBV) in human hepatocellular carcinoma (Beasley et al, In: Vyas G N, Dienstag J L, Hoofnagle J H, eds. Viral hepatitis and liver disease. Orlando, Fla., Grune and Stratton, 1984, 209–224). These observations, together with the correlation of retroviral infection such as HTLV-I in Adult T-cell leukemia asserts the possible role of infectious viruses acting as transducing agents in the pathogenesis of these aforementioned human neoplasms and disorders.

The mechanism(s) by which infectious viruses exert their oncogenicity is believed to be mediated by DNA recombination with the host cell DNA. The mammalian genome contains certain genes, designated proto-oncogenes, that can acquire oncogenic properties upon transduction into the genome of acute transforming retroviruses (Bishop, Ann. Rev. Biochem. 1983, 52:301; Bishop, Cell 1985, 42:23). In certain human cancers (e.g. T24 and EJ human bladder carcinoma) it has been well documented that the identified transforming gene (H-ras-1 locus) relates to the v-rasH of the Harvey murine sarcoma virus. Among the proto-oncogenes and oncogenes, the ras family has been thoroughly characterized and studied with respect to activation and expression in human neoplasms. When a proto-oncogene undergoes point-mutation (e.g. c-rasH) or rearrangement (e.g. n-myc), such changes can lead to a loss of cell regulation in differentiation and growth, and eventually oncogenesis.

Recently, a transforming DNA sequence from a human (Mahlavu) hepatocellular carcinoma, $hhc^M$, has been identified and molecularly cloned as part of a large fragment (Yang et al, J. Gen. Virol. 1982, 63:25; Yang et al, Environmental Health Perspectives 1985, 62:231). A number of $hhc^M$ related DNA clones from several other human hepatocellular carcinomas have been isolated that exhibited nil to moderate cell transforming activity on NIH/3T3 cells. Two have been partially characterized and they are a moderately cell-transforming gene from Mahlavu hepatocellular carcinoma ($hhc^M$) and a putative cellular homologue (c-hhc) isolated from normal human liver DNA, which has no cell-transforming activity. The biological activities of two molecular clones of $hhc^M$ and a Korean $hhc^M$ and c-hhc have been characterized and compared (Yang et al, Leukemia 1988, 2(12 Supplement):102S). Amplification of the $hhc^M$ sequence in the various genomic DNAs of hepatomas from 2 Chinese, one African and 17 Korean sources, was observed and compared with the distribution of integrated HBV DNA sequences in the same hepatomas in order to provide some insight into the possible role of $hhc^M$.

The present invention relates to an oncoprotein specific for hepatocellular carcinomas and to a nucleotide sequence that codes for such a protein. The invention further relates to diagnostic and screening methodologies (and kits based thereon) that make use of the oncoprotein (or antibodies specific for same) and the nucleotide sequence.

SUMMARY OF THE INVENTION

It is one object of the invention to provide a hepatocellular oncoprotein and a nucleotide sequence coding for same.

It is another object of the invention to provide a diagnostic test for the presence of hepatocellular carcinomas as well as preneoplastic or pathological conditions of the liver.

Further objects and advantages of the present invention will be clear to one skilled in the art from the description that follows.

In one embodiment, the present invention relates to a DNA fragment coding for the amino acid sequence set forth in FIG. 1 or an allelic variation of that sequence, or a unique portion thereof.

In another embodiment, the present invention relates to a recombinant DNA molecule comprising:
  i) a vector, and
  ii) the above-described DNA fragment.

In a further embodiment, the present invention relates to a host cell transformed with the above-described recombinant DNA molecule.

In another embodiment, the present invention relates to a nucleotide fragment sufficiently complementary to the above-described DNA fragment to hybridize therewith.

In a further embodiment, the present invention relates to a protein having the amino acid sequence set forth in FIG. 1 or an allelic variation of that sequence, or a unique portion thereof.

In another embodiment, the present invention relates to antibodies (polyclonal and/or monoclonal) specific for the above-described protein.

In a further embodiment, the present invention relates to a process of producing the above-described protein comprising culturing a host cell transformed with the above-described recombinant DNA molecule under conditions such that the DNA fragment is expressed and the protein thereby produced; and isolating the protein.

In another embodiment, the present invention relates to a method of detecting the presence of the above-described protein in a sample comprising:
  i) contacting the sample with an antibody specific for the protein under conditions such that binding of the antibody to the protein can occur, whereby a complex is formed; and
  ii) assaying for the presence of the complex.

In another embodiment, the present invention relates to a method of detecting the presence of a nucleotide sequence coding for the above-described protein in a sample comprising:
  i) contacting the sample with a nucleotide fragment sufficiently complementary to the nucleotide sequence to hybridize therewith under conditions such that hybridization can occur, whereby a complex is formed, and ii) assaying for the presence of the complex.

In a further embodiment, the present invention relates to a method of diagnosing the presence of hepatocellular carcinoma in a patient comprising:

i) contacting a biological sample from the patient with the above-described antibody under conditions such that binding of the antibody to the protein present in the sample can occur, whereby a complex is formed; and ii) assaying for the presence of the complex.

In another embodiment, the present invention relates to a method of diagnosing the presence of hepatocellular carcinoma in a patient comprising:

i) contacting nucleic acid sequences derived from a cellular sample from the patient with the above-described nucleotide fragment under conditions such that hybridization can occur, whereby a complex is formed; and ii) assaying for the presence of the complex.

In another embodiment, the present invention relates to a diagnostic kit for detecting the presence of the above-described protein in a sample comprising a container means having disposed therewithin antibodies specific for the protein.

In a further embodiment, the present invention relates to a diagnostic kit for detecting the presence of a nucleic acid sequence coding for a protein having the amino acid sequence set forth in FIG. 1 or an allelic variation of the sequence, or a unique portion thereof, comprising a container means having disposed therewithin the above-described nucleotide fragment.

BRIEF DESCRIPTION OF THE FIGURES

FIG. 1: Complete nucleotide sequence of hhc$^M$, and the amino acid sequence of a 52,000 dalton protein encoded within its open reading frame.

FIG. 6: (B) Reactivity of a polyclonal anti-p52. Anti-p52 polyclonal IgG was raised by immunizing rabbits. SDS polyacrylamide gel purified p52 at 0.8 to 1.0 mg each was used to immunize the New Zealand White rabbit by standard techniques. Two booster injections were given. Detergent (0.2% SDS) lyzed samples corresponding to 0.2 ml of packed human hepatoma cells (1/3:v/v) including Mahlavu hepatocellular carcinoma, Hp3p21.7 and HPG2, and pB$^r$pM-1 transfected BRL-1 tumor cells and control BRL-1 cells and p52, at 10 μl each were applied to sample well and allowed to diffuse and cross-react overnight against the polyclonal anti-p52 IgG. Results were recorded at 48 hours.

DETAILED DESCRIPTION OF THE INVENTION

Figure 2:
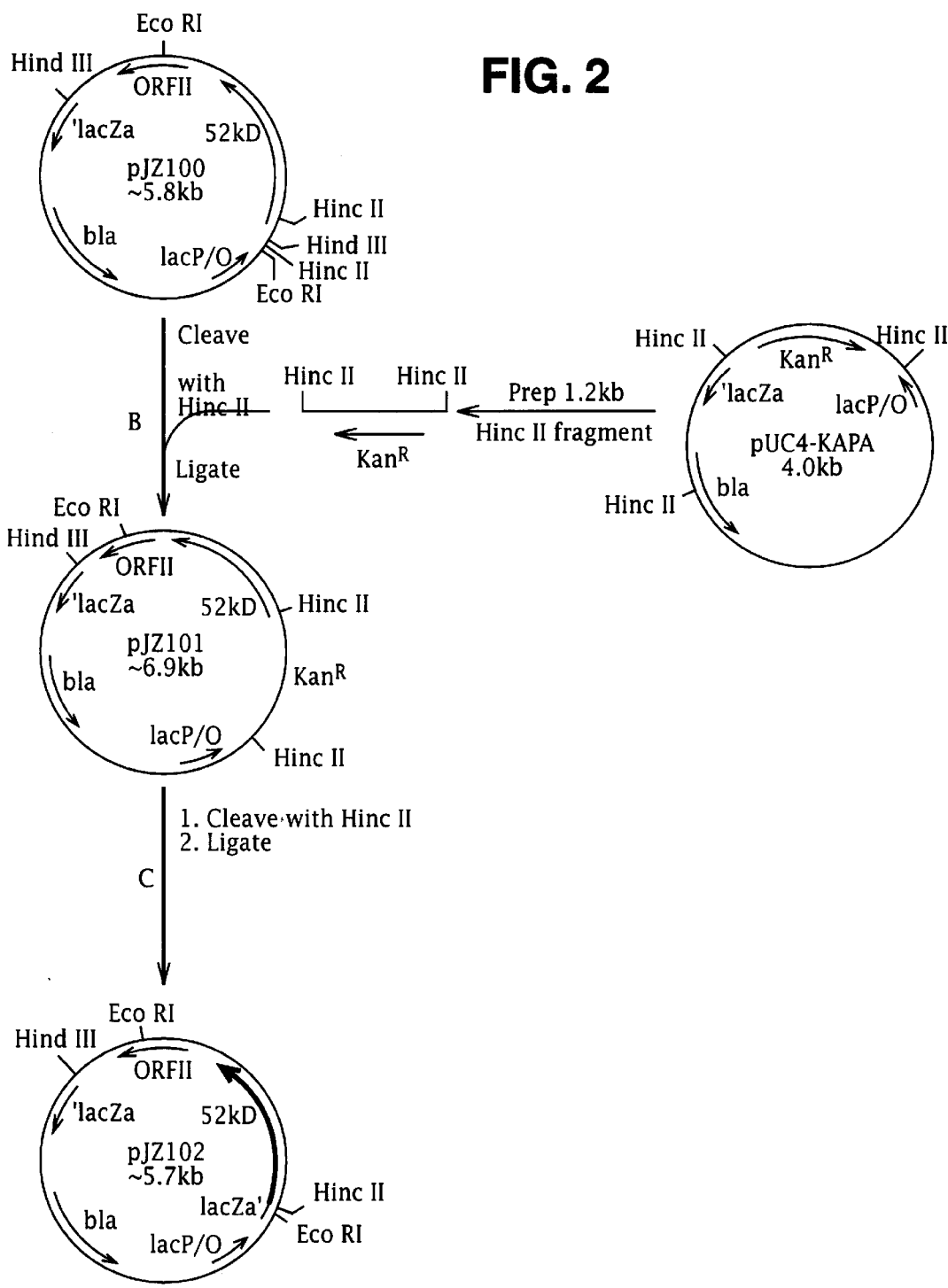
FIG. 2: Construction of hhc$^M$-LacZ chimeric plasmid for the production of the hhc$^M$ 52 kD protein.

The present invention relates to an oncoprotein coded for by a transforming nucleotide sequence of hepatocellular carcinomas and to the transforming sequence itself. The invention further relates to unique portions (i.e., at least 5 amino acids) of the oncoprotein, and to nucleotide sequences (fragments) that code for such polypeptides. The invention further relates to nucleotide segments sufficiently complementary to the above-described nucleotide sequences (fragments) to be used as probes for detecting the presence of such nucleotide sequences (fragments). The invention also relates to diagnostic and screening methodologies for use in detecting the presence of hepatocellular carcinomas (as well as preneoplastic or pathological conditions of the liver) in a warm blood animal.

The oncoprotein of the present invention is an amplified gene expression product of hepatoma cells that is specifically related to hepatomas. The protein can have the complete sequence given in FIG. 1, in which case it is designated hhc$^M$. The protein can also have the amino acid sequence of a molecule having substantially the same properties (e.g., immunological) as the molecule given in FIG. 1 (for example, allelic forms of the FIG. 1 sequence). Alternatively, the protein (or polypeptide) of the invention can have an amino acid sequence corresponding to a unique portion of the sequence given in FIG. 1 (or allelic form thereof).

The protein can be present in a substantially pure form, that is, in a form substantially free of proteins and nucleic acids with which it is normally associated in the liver. The oncoprotein of the invention, including that made in cell-free extracts using corresponding mRNA, and the oncoprotein made using recombinant techniques, can be purified using protocols known in the art. The oncoprotein, or unique portion thereof, can be used as an antigen, in protocols known in the art, to produce antibodies thereto, both monoclonal and polyclonal.

In another embodiment, the present invention relates, as indicated above, to nucleotide sequences (fragments) (including cDNA sequences) that encode the entire amino acid sequence given in FIG. 1 (the specific DNA sequence given in FIG. 1 being only one example), or any unique portion thereof. Nucleotide sequences to which the invention relates also include those coding for proteins (or polypeptides) having substantially the same properties (e.g., immunological) of the hhc$^M$ polypeptide (for example, allelic forms of the amino acid sequence of FIG. 1). The invention further relates to nucleotide segments sufficiently complementary to the above-described nucleotide sequences (fragments) to hybridize therewith (e.g. under stringent conditions).

In another embodiment, the present invention relates to a recombinant molecule that includes a vector and a nucleotide sequence (fragment) as described above (advantageously, a DNA sequence coding for the molecule shown in FIG. 1 or a molecule having the properties thereof). The vector can take the form of a virus or a plasmid vector. The sequence can be present in the vector operably linked to regulatory elements, including, for example, a promoter (e.g., the LacZ promoter). The recombinant molecule can be suitable for transforming procaryotic or eucaryotic cells, advantageously, protease deficient $E.$ $coli$ cells.

A specific example of a recombinant molecule of the invention is shown in FIG. 2. In this example, the hcc$^M$ nucleotide sequence is placed in a chimeric construct by replacing the codons of the original N-terminus 18 amino acids of the hhc$^M$ p52kD with the procaryote LacZ expression/translation sequence plus codons for 11 amino acids by appropriate recombinant DNA manipulations (Yang et al. Proc. of the XIV Inter. Symp. Sponsored by the International Association for Comparative Research on Leukemia and Related Diseases November 1989 (Vale, Colo.)). Driven by the LacZ promoter, the resultant chimeric gene is expressed at high levels in a protease deficient $E.$ $coli$ mutant at 30° C. In a further embodiment, the present invention relates to a host cell transformed with the above-described recombinant molecule. The host can be procaryotic (for example, bacterial (advantageously $E.$ $coli$)), lower eucaryotic (i.e., fungal, including yeast) or higher eucaryotic (i.e. mammalian, including human). Transformation can be effected using methods known in the art. The transformed host cells can be used as a source for the nucleotide sequence described above (which sequence constitutes part of the recombinant molecule). When the recombinant molecule takes the form of an expression system (see specific construct described above), the transformed cells can be used as a source for the oncoprotein.

The oncoprotein and nucleic acid sequence of the present invention can be used both in a research setting (for example, to facilitate an understanding of how and why hepatocellular carcinomas develop) and in a clinical setting to, for example, diagnosis (and/or screening) the presence and/or progress of hepatocellular carcinomas (as well as preneoplastic or pathological condition of the liver).

The diagnostic/screening methodologies referred to above can be carried out using antisera or monoclonal antibodies (produced using known techniques) against the oncoprotein (or unique portions thereof) of the invention. For example, the diagnostic method can take the form of an immunoassay that can be used with urine or serum samples of patients at high risk for hepatocellular carcinoma (e.g. chronic hepatitis carriers) and/or of populations in the geographically identified hot-spots of liver cancer (e.g. Chitung Province of China). The screening immunoassay can be of the simple dip-stick type where binding of one member of the antigen/ antibody pair, attached to the stick, with the other member of the pair, present in the sample, is accompanied by a color change (such dip-stick type assays have been described for use with a variety of binding pairs). Such simple tests would be easily and widely applicable to populations in areas where analytical electrophoresis equipment (required for detecting alpha-fetoprotein levels in patients' sera, which levels are currently used in screening and diagnosing the presence of hepatocellular carcinomas) may not be readily available.

The diagnostic methods of the invention can also take the form of a histochemical diagnostic tests involving the use of antibodies against the protein or polypeptide of the invention. Such a test can be used on frozen or prefixed liver thin section samples to enable a more definite diagnosis of liver cancer.

The diagnostic methods of the invention can also involve the use of nucleic acid probes sufficiently complementary to a portion of the nucleic acid sequence of the invention to hybridize thereto. Such probes can be used to detect the presence of the endogenous sequence, for example, following electrophoresis of genomic DNA digested with appropriate restriction enzymes. The probe can be labelled, for example, with 32P, to facilitate detection.

The invention further relates to diagnostic/screening kits for use in carrying out the above methods. The kits can comprise, for example, the above-described antibodies specific for the oncoprotein (or polypeptide) of the invention or, alternatively, the above-described nucleic acid probes, together with any ancillary reagents (e.g., buffers, detectable markers, enzyme substrates, etc.) necessary to conducting the test.

The invention is described in further detail in the following non-limiting Examples.

EXAMPLES

The following protocols are referenced in the Examples that follow:

Molecular cloning of hhc$^M$

Genomic DNA purified from human normal liver and Mahlavu (African) hepatocellular carcinoma (HHC), as described below, were subjected to complete digestion by HindIII restriction endonuclease. (Other restriction endonucleases including BamHI, EcoRI and PstI, were also used for isolating genomic DNA fragments from HHC and liver DNA in an attempt to clone HHC DNA sequences; the clones isolated from these efforts were not successful with respect to transfection studies.) The DNA samples both [$^3$H]aflatoxin B. (AFB$_1$)-epoxide bound (as described below) and unbound, were separated into 180 fractions by polyacrylamide gel electrophoresis. Specificity of [$^3$H] AFB$_1$-epoxide per μg of DNA was determined. Fractions with significant [$^3$H]AFB$_1$-epoxide specific activity were used in DNA transfection assay on NIH3T3 cells as described below. Fractions showing positive focus formation indicating positive cell transformation, were identified and the parallel unbound DNA fractions were molecularly cloned by ligation onto the HindIII site of pBR322, pBR325 and/or Puc 8 plasmid DNAs for transformation of $E.$ $coli$ HB101 cells as described elsewhere (Yang et al., J. Gen.

Virol. 1982, 63:25). Primary selection of the resultant clones was thus based on (1) the sensitivity to tetracycline, and/or color change associated with the disruption of the lacz operon containing the B-galactosidase coding sequence of the plasmid; and (2) the capability of cell-transformation in transfection assays on NIH3T3 cells with or without $AFB_1$ binding; (3) the presence of human sequence in colony-hybridization and DNA-DNA hybridization against [$^{32}$P] probes prepared from human Alu sequence (Lawn et al., Cell 1978, 15:1157) and also [$^{32}$P] labelled HindIII digested MAH HHC DNA fragments; and (4) [$^3$H] $AFB_1$-epoxide binding on the DNA fragments. After screening over 30,000 clones by these quadruple technical approaches including [$^3$H]$AFB_1$ binding, transfection assay on NIH3T3 cells and DNA-DNA hybridization against the [$^{32}$P]Alu and [$^{32}$P] HindIII MAH HHC DNA probes, three clones were isolated. One particular 3.1 kb DNA restriction fragment constitutes the $hhc^M$ DNA.

Preparation of plasmid DNA and $AFB_1$ binding

The clone used in these studies has been referred to as PM-1. Plasmid DNA was prepared by the Holmes' method, i.e. the rapid heating method, followed by $CsCl_2$-ethidium bromide isopycnic centrifugation at 180,000×g for 20 hrs (Maniatis et al., Molecular Cloning, Cold Spring Harbor Laboratory, Cold Spring Harbor, N.Y. 1982). The banded PM-1 DNA was then purified free of ethidium bromide by isopropanol extraction and exhaustive dialysis against TEN buffer. A yield of 25 to 50 $\mu$g of total plasmid DNA per 5 ml of culture was generally obtained. The 3.1 kb $hhc^M$ DNA was then separated from PUC 8 DNA and other contaminants by digesting the PM-1 DNA with HindIII endonuclease and then subjecting to agarose gel electrophoresis and electroelution of the separated 3.1 kb band. The resultant 3.1 kb $hhc^M$ DNA was homogeneously purified and used in $AFB_1$ activation experiments.

The $hhc^M$ 3.1 kb DNA was also cloned into a pSV-neo vector that carried a murine retroviral (Moloney) LTR, SV40 promoter and part of the T antigen besides the neomycin resistance gene. This clone, rpMpN-1, is expressed at a significantly higher level when transfected into cells and offers special advantages for transfection assay.

[$^3$H]$AFB_1$ at 15 Ci/mmole specificity was acquired from Morales Laboratory, Calif. It was further purified by HPLC to homogeneity and the resultant single peak of [$^3$H]$AFB_1$ had the specific activity of 9,250 cpm/pmole. It was used in activation reactions with either mixed function oxidases freshly prepared from liver microsomal preparation or by the chemical peroxidation reaction using perchlorobenzoic acid and methylene chloride as described earlier (Bennett et al., Cancer Res. 1981, 41:650; Garner et al., Chem. Biol. Interact. 1979, 26:57). Binding of [$^3$H]$AFB_1$ epoxide with either high molecular weight HHC or plasmid DNA was monitored by kinetic analysis (Yang et al. Environmental Health Perspective 1985, 62:231 and Modali and Yang, Monitoring of Occupational Genotoxicants pp. 147–158 (1986)). Samples withdrawn at each time point was washed free of unbound ($^3$H)$AFB_1$ epoxide with chloroform, and ethanol precipitated prior to redissolving the [$^3$H]$AFB_1$-DNA in Tris-EDTA-NaCl (TEN) buffer for transfection assay or sequence analysis.

Cells, tissue culture and transfection assay

NIH/3T3 cells, passage 6 to 11, and Buffalo rat liver cells (BRL-1) for transfection assays, were maintained in Dulbecco's modified Eagle's media supplemented with 10% heat-inactivated fetal calf serum, penicillin (50 units $ml^{-1}$) and streptomycin (25 $\mu$g $ml^{-1}$) (DMEM) in a 5% $CO_2$ atmosphere, at 37° C.

DNA transfection was carried out as described earlier (see Yang et al. 1985 and Modali and Yang 1986, referenced above). Optimal conditions were achieved by carefully titrating the pH curve for the DNA-calcium phosphate complex mixture; it was usually found that pH 6.75 ensured a fine complex precipitation.

Preparations of DNA and RNA from tissue culture cells and tumor tissues

Total high molecular weight (HMW) DNA was extracted and purified from tissue culture cells and tumor tissues as described elsewhere (Yang et al., 1985 referenced above). The HMW DNA thus purified, has been subjected to proteinase K digestion, first sequential chemical purification with phenol-cresol, chloroform-isoamyl alcohol, ether and ethanol-NaCl precipitation, followed by RNase digestion and a second sequential chemical purification. The purified DNAs were then dialyzed against TEN buffer for use in experiments. Total RNA was extracted from tissue culture cells and prepared as described previously (Maniatis et al., 1982 referenced above). Poly A rich RNA was obtained by affinity separation with oligo dT cellulose (Collaborative Research, Mass.) column elution.

Tumorigenesis

Transformed cells, cloned out from the transfected cell culture by either cloning cylinder method or terminal dilution method, were expanded and inoculated at $10^4$ to $10^6$ cells into athymic Swiss nu/nu mice subcutaneously. Tumorigenesis in the challenged mice was monitored closely.

Nucleotide sequence analysis and site-targeted mutagenesis

Nucleotide sequencing of the $hhc^M$ 3.1 kb and variants produced by site-targeted mutagenesis were carried out by the standard Maxam-Gilbert Methods in Enzymology 1980, 65:499 and the Sanger (M13) dideoxy sequencing methods (Maniatis et al., 1982 referenced above).

Specified oligonucleotide sequence of 20 mers carrying the targeted dG→T mutation were synthesized by the Applied Biosystem oligonucleotide synthesizers. They were used as templates in generating the mutated clones. Mutant DNA clones were produced in accordance with the protocol provided by and using the oligonucleotide-directed in vitro system of Amersham (Arlington Hts., Ill.). DNAs of the mutated clones were verified by nucleotide sequencing. Effects of these site-targeted mutagenized DNA were analyzed by potentiation of cell-transformation in transfection assay on NIH/3T3 cells and RNA expressions in transfected cells using the BRL dot-blot technique (Bethesda Research Laboratory, Rockville, Md.).

EXAMPLE I

Figure 3:
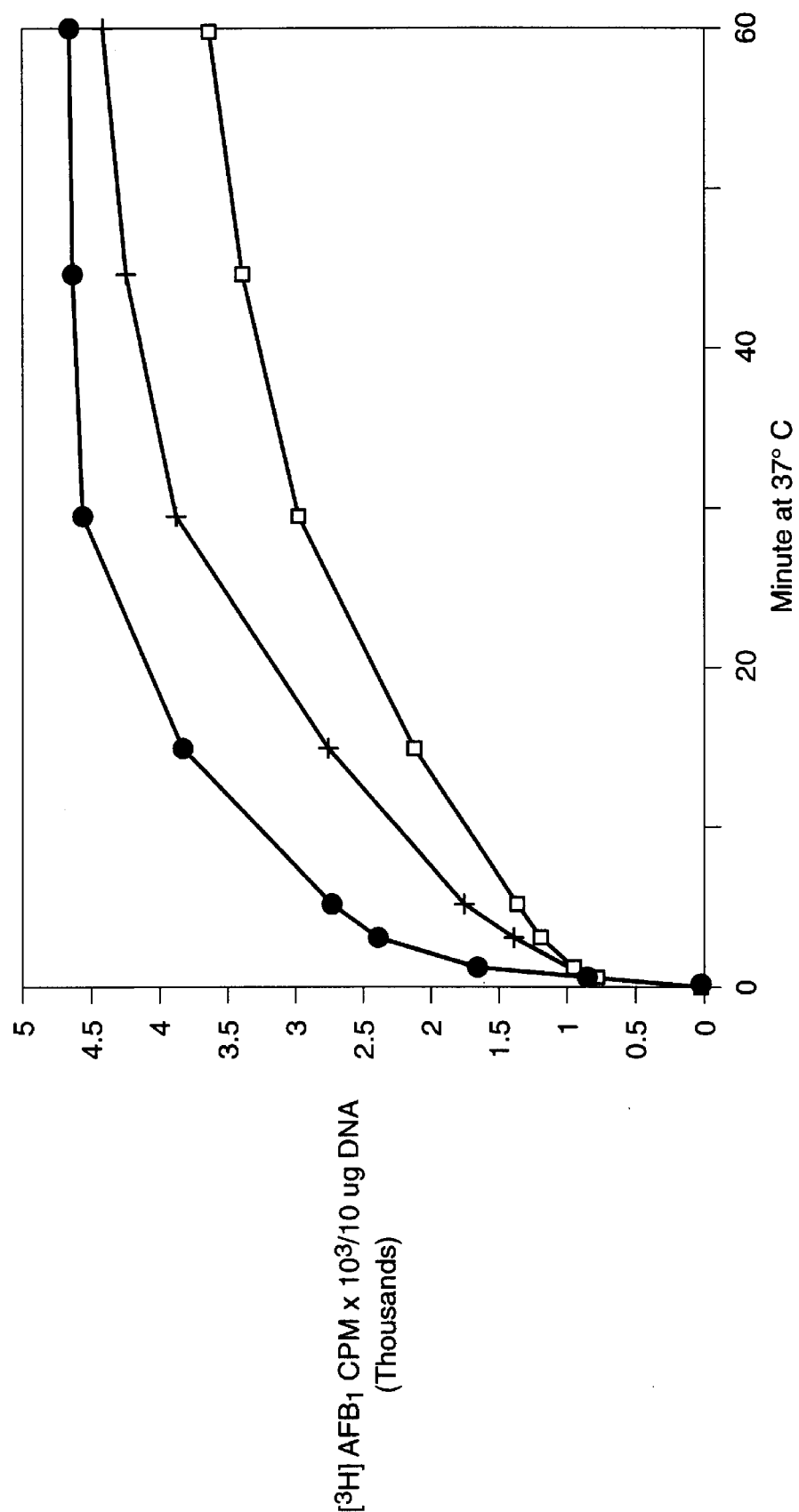
FIG. 3: Aflatoxin B$_1$ epoxide binding on high molecular weight DNAs prepared from human hepatocellular carcinoma (Mahlavu), human normal liver and from murine (NIH/3T3) fibroblasts.
Figure 4:
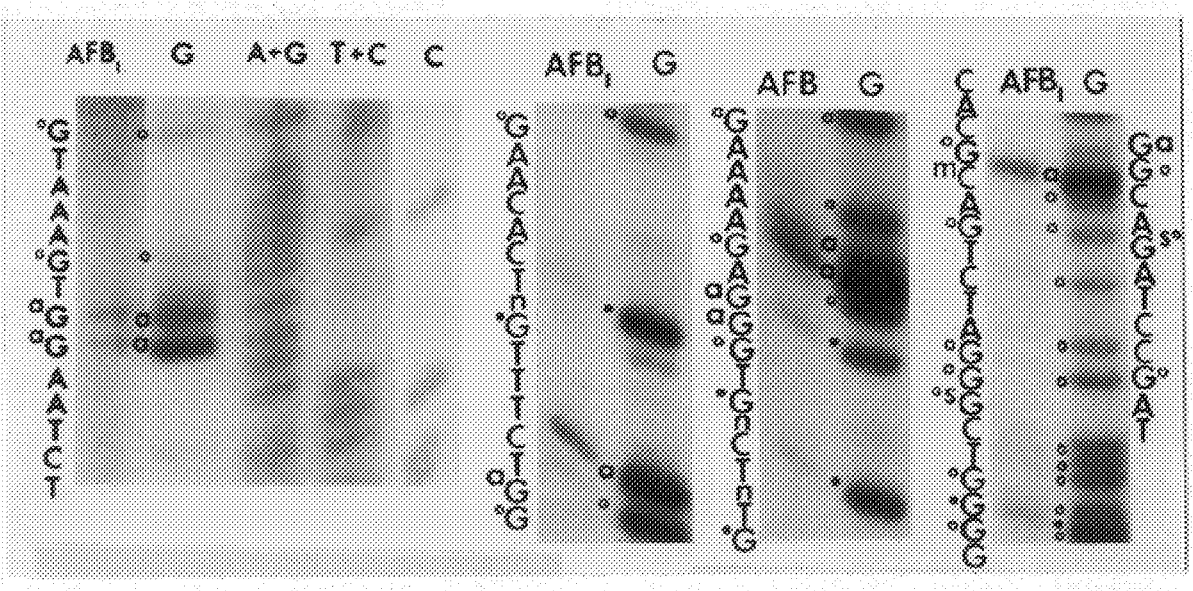
FIG. 4: Identification of the dG bound by AFB$_1$ epoxide within the hhc$_M$ (PM-1) DNA by a modified Maxam-Gilbert sequencing method. Nucleotide sequences are specified on the side. The left panel illustrates ladder for all four deoxynucleotides and AFB$_1$-dG; only native dG and AFB$_1$-dG were given in all other three panels on the right, aG=AFB$_1$ bound dG at all time; °G=dG that was not reacted with AFB$_1$; whereas °G=moderately preferred dG.

Dosimetry of $AFB_1$ binding and potentiation of $hhc^M$ cell-transformation capability on NIH/3T3 cells $AFB_1$ epoxide binds high molecular weight DNAs prepared from human hepatoma, human liver and mouse NIH/3T3 cells efficiently (FIG. 3). The initial rates in each binding kinetic were extremely rapid. The rates of $AFB_1$-epoxide binding to human normal liver or hepatoma DNA and to murine NIH/3T3 cell DNA became significantly different after one minute of binding reaction. The MAH HHC DNA showed a greater rate of binding than normal liver DNA and all the dG targets became saturated earlier, whereas $AFB_1$ epoxide bound the normal liver DNA at a slower rate but eventually saturated all the dG targets at a slightly lower level. The human DNAs showed a higher level of $AFB_1$ binding than the murine NIH/3T3 cell DNA. The overall $AFB_1$ specific activity, i.e. $AFB_1$-dG adduct, was found to be about one dG bound per 10 nucleotides among these high molecular weight double stranded DNAs. This overall specificity also took into consideration the existence of secondary or tertiary structure of the high molecular weight DNAs. $AFB_1$ epoxide binding on linearized 3.1 kb double stranded $hhc^M$ DNA was consistently found to be 4 to 8 dG bound per $10^4$ nucleotides. This higher binding capability reflects the relatively easy accessibility of dG within the linearized double stranded PM-1 DNA by $AFB_1$ epoxide and should not be compared with the efficiency of $AFB_1$-dG adduct formation with high molecular weight native double-stranded DNA.

Within a finite dosimetry the binding of $AFB_1$ epoxide with dG potentiates the cell-transformation capability of $hhc^M$ by 10 to 20 fold as seen in the experiment illustrated in Table 1.

TABLE 1

$AFB_1$ Dose-dependent Activation of PM-1 DNA in The transformation of NUH/3T3 cells

| DNA Source | $AFB_1$ femtomole per 100 ng DNA | Number of Foci per 100 ng DNA |
|---|---|---|
| $hhc^M$ (PM-1) | 0 | $15 \times 10^{-1}$ |
| c-Ha-ras-1 | 0 | 465 |
| c-K-ras-1 | 0 | 0 |
| c-hhc (human liver homolog) | 0 | 0 |
| E. coli | 0 | 0 |
| $hhc^M$ (PM-1) | 0 | $15 \times 10^{-1}$ |
|  | 5 | 18 |
| $hhc^M$ (PM-1) | 14 | 26 |
|  | 24 | 66 |
|  | 35 | 3 |
| c-hhc | 0 | 0 |
|  | 8 | 0 |
|  | 15 | 0 |
|  | 30 | 0 |
|  | 40 | 0 |

$AFb_1$ binding and transfection assay were as described in Methods. Data were calculated on the basis of per 100 ng. In the assay with unbound $hhc^M$ DNA the transfection assays were carried out with 500 ng to 1.5 ug of DNA in order to obtain reasonable foci formation on NIH/3T3 cells. Transfection with $AFB_1$-epoxide bound DNA was carried out at a range of 50 to 500 ng DNA. Data were normalized to show potentiation of $hhc^M$ cell-transformation capability by $AFB_1$-epoxide activation.

Whereas the efficiency of unbound PM-1 DNA in transforming NIH/3T3 cells was usually observed at about 15 FFU/$\mu$g DNA the efficiency of $AFB_1$ epoxide activated PM-1 DNA was optimized at 66 FFU/100 ng DNA, an increase of 20 fold. The possibility of non-specific mutagenization accounting for this potentiation were considered. That this potentiation effect was due to free $AFB_1$ that diffused into the cell or recycling of $AFB_1$ adducts has been ruled out earlier with the appropriate control experiments which showed that activation of normal liver or E. coli DNA at the same dosimetry failed to activate any cell-transforming capability (Yang et al., 1985 referenced above). Moreover in this experiment with $AFB_1$ activated DNA from c-$ras^k$-1 or c-hhc, a normal human liver homolog to $hhc^M$ as the appropriate controls, no cell-transformation of NIH/3T3 cells was obtained suggesting that $AFB_1$ epoxide activated PM-1 DNA was not a random phenomenon. Moreover the $AFB_1$ dose-dependency of PM-1 DNA in cell-transformation efficiency (Table 1) further substantiated the specificity of $AFB_1$ epoxide binding in conferring the potentiation of cell-transformation. Whereas optimal dosimetry was seen at 24 femtomole $AFB_1$/100 ng of PM-1 DNA, at dosimetry beyond 45 femtomole per 100 ng of PM-1 DNA, an overkill effect was observed. No transformed foci were obtained in NIH/3T3 cells transfected with $AFB_1$ epoxide bound PM-1 DNA although human DNA was incorporated into the NIH/3T3 cells in a degraded form (Yang et al., 1985 and Modali and Yang, 1986 referenced above). This observation suggested that over activation of PM-1 DNA not only generated scissions in the molecule but possibly degradation leading to a loss of biological activity. It was also evident from these results that no more than one or at most a few $AFB_1$-dG adducts per PM-1 DNA molecule could be tolerated by the $hhc^M$ DNA before the biological activity of the $hhc^M$ DNA became compromised and at the risk of survival. Moreover the potentiation of $hhc^M$ DNA in cell-transformation probably necessitates no more than one or at most a finite number of $AFB_1$ bindings.

EXAMPLE II

Specificity of the $AFB_1$-epoxide binding on dG's of PM-1 DNA

Deoxyguanine nucleotide of native DNA, when bound by $AFB_1$ epoxide, became alkali and therefore could be identified by piperidine cleavage; whereas unbound deoxyguanine nucleotide within the same native DNA would not cleave without dimethyl sulfide (alkali) treatment. FIG. 4 shows the dG targets within the PM-1 DNA when bound at a saturation conditions. When the targeted sequences are evaluated in sets of tetranucleotides, an empirical formulation can be derived on the basis of the binding pattern of $AFB_1$ epoxide with the dG's in PM-1 DNA. Table 2 summarizes the nucleotide sequence in a set of tetranucleotides that were seen and targeted by $AFB_1$ epoxide. As shown in FIG. 4, the dG within a sequence of any one of the following tetranucleotides of AGAG, AGTT, TGTT, TGAT, or AGAA, escaped attack by $AFB_1$ epoxide and hence showed no cleavage in the sequence without prior DMS treatment. This is confirmed by the distinct cleavage of dG as a result of $AFB_1$ epoxide attack on dG in a sequences of GGGC, CGGC, AGGC, TGGC or CGCG. Upon evaluating the various sequences in which a dG target could be accessed by $AFB_1$ epoxide, it can be concluded that within a double stranded DNA, the least likely dG target would be that flanked by dA and dT, i.e. category III. The most likely dG target would be that flanked by dG and/or dC, i.e. category I, and that tetranucleotide sequences in which dG is either preceded by dA or T and followed by dG and dC would be the moderately preferred targets of $AFB_1$ epoxide, i.e. category II. This, of course, does not take into consideration the secondary or the tertiary structure of the DNA in its natural state since these analyses were done on linearized double-stranded DNA. It should also be mentioned that whereas the dG binding affinity of $AFB_1$-epoxide was greatly affected by the vicinal nucleotides in the double-stranded PM-1 DNA, no specificity was observed with respect to $AFB_1$-epoxide binding to dG in single stranded DNA. The observations of Modali and Yang (1986 referenced above) were basically in agreement with others working on $AFB_1$ binding on ØX174 and pBR 322 DNAs (Misra et al., Biochemistry, 1983, 22:3351).

TABLE 2

Vicinal Nucleotide Sequence Dictates The dG Targets of $AFB_1$-Epoxide Binding*

| Preferred Targets Category I | Least Favored Targets Category III |
|---|---|
| * | * |
| GGCC | ACAG |
| GGCC | ACTC |
| CGGA | ACAA |
| GGCT | ACAC |
|  | ACAT |
| CGGC | TCAG |
| AGGC | TCAC |
| TGGG | TGAA |
|  | TGAC |
| CGGC | TGTG |
| AGGC | TGTA |
| TGGC | TGTC |
| CGGA | TGTT |
| AGGA |  |
| TGGA |  |
| CGGT |  |
| AGGT |  |
| TGGT |  |

TABLE 2-continued

Vicinal Nucleotide Sequence Dictates The dG Targets of $AFB_1$-Epoxide Binding*

| Preferred Targets Category I | Least Favored Targets Category III |
|---|---|

*This table represents the dG targets of $AFB_1$-epoxide binding observed in studies with linearized double stranded PM-1 DNA. Moderately preferred dG targets, i.e. Category II, are omitted here but are described elsewhere (Modali and Yang, 1986).

Within the past two years, the nucleotide sequence of $hhc^M$ has been resolved by a combination of Maxam-Gilbert nucleotide sequencing technique and the M13 dideoxy method using the BRL kilobase sequencing system. Applying these empirical rules in computer analysis of the $hhc^M$ 3.1 kb nucleotide sequence, the most and moderately preferred dG targets within the various loci of $hhc^M$ have been predicted (Table 3). Although a maximum number of 60 dG targets was predicted on the basis of $AFB_1$-epoxide binding studies with linearized 3.1 kb $hhc^M$ DNA, it was evident upon examining the possible secondary and tertiary structure of $hhc^M$ sequence, that a much lower number of dG targets would be accessible by $AFB_1$-epoxide. Moreover, only a few such induced mutations would produce any effect of survival value.

TABLE 3

Predicted dG Targets within The Nucleotide Sequence of $hhc^M$ Preferrentailly Attacked by $AFB_1$-Epoxide

| * CGCC | * CGGC | * GGCC | * GGGC | * GGGA | * AGGA | * TGCC | * TGCG | * TGGA | * TGGG | * GGAG |
|---|---|---|---|---|---|---|---|---|---|---|
|  | * CGGC |  |  | * GGGA | * AGGA |  |  | * TGGA | * TGGG |  |
|  |  |  |  | 73 |  |  |  |  |  |  |
|  |  |  |  | 74 |  |  |  |  |  |  |
|  |  |  |  |  | 84 |  |  |  |  |  |
|  |  |  |  |  |  |  |  |  | 97 |  |
|  |  |  |  |  |  |  |  |  | 98 |  |
|  |  |  |  | 125 |  |  |  |  |  |  |
|  |  |  |  | 126 |  |  |  |  |  |  |
|  |  |  |  |  |  |  |  |  |  | 140 |
|  |  |  |  |  |  |  |  | 221 |  |  |
|  |  |  |  |  | 223 |  |  |  |  |  |
|  |  |  |  |  | 224 |  |  |  |  |  |
|  |  |  |  |  | 307 |  |  |  |  |  |
|  |  |  |  |  | 308 |  |  |  |  |  |
|  |  |  |  |  |  |  |  | 371 |  |  |
|  |  |  |  |  |  |  |  | 391 |  |  |
|  |  |  | 472 |  |  |  |  |  |  |  |
|  |  |  |  |  |  |  |  |  | 481 |  |
|  |  |  |  |  |  |  |  |  | 492 |  |
|  |  |  |  | 494 |  |  |  |  |  |  |
|  |  |  |  | 495 |  |  |  |  |  |  |
|  |  |  |  |  | 539 |  |  |  |  |  |
|  |  |  |  |  |  |  |  |  |  | 550 |
|  |  |  |  | 560 |  |  |  |  |  |  |
|  |  |  |  | 561 |  |  |  |  |  |  |
|  |  |  | 577 |  |  |  |  |  |  |  |
|  |  |  |  | 692 |  |  |  |  |  |  |
|  |  |  |  |  |  |  |  |  | 860 |  |
|  |  |  |  |  | 901 |  |  |  |  |  |
|  |  |  |  |  | 1125 |  |  |  |  |  |
|  |  |  |  | 1320 |  |  |  |  |  |  |
|  |  |  |  | 1321 |  |  |  |  |  |  |
|  |  |  |  |  |  |  |  | 1330 |  |  |

TABLE 3-continued

Predicted dG Targets within The Nucleotide Sequence of hhc<sup>M</sup> Preferrentailly Attacked by AFB₁-Epoxide

| CGCC | CGGC | GGCC | GGGC | GGGA | AGGA | TGCC | TGCG | TGGA | TGGG | GGAG |
|------|------|------|------|------|------|------|------|------|------|------|
|      | *    |      |      | *    | *    |      |      | *    | *    |      |
|      | CGGC |      |      | GGGA | AGGA |      |      | TGGA | TGGG |      |
|      |      |      |      |      |      |      |      | 1354 |      |      |
|      |      |      |      |      |      |      |      | 1404 |      |      |
|      | 1405 |      |      |      |      |      |      |      |      |      |
|      |      |      |      | 1431 |      |      |      |      |      |      |
|      | 1543 |      |      |      |      |      |      |      |      |      |
|      | 1588 |      |      |      |      |      |      |      |      |      |
|      |      |      |      |      |      |      |      |      | 1637 |      |
|      |      |      |      |      | 1652 |      |      |      |      |      |
|      |      |      |      | 1765 |      |      |      |      |      |      |
|      |      |      |      |      | 1815 |      |      |      |      |      |
|      | 1853 |      |      |      |      |      |      |      |      |      |
|      |      |      |      |      | 1862 |      |      |      |      |      |
|      |      |      |      |      |      |      |      |      |      | 1868 |
|      |      |      |      |      |      |      | 1878 |      |      |      |
|      |      |      |      | 1986 |      |      |      |      |      |      |
|      |      |      |      | 2064 |      |      |      |      |      |      |
|      |      |      |      |      | 2094 |      |      |      |      |      |
|      | 2205 |      |      |      |      |      |      |      |      |      |
|      |      |      |      |      |      |      |      | 2315 |      |      |
|      |      |      |      |      |      |      |      | 2331 |      |      |
|      |      |      |      | 2352 |      |      |      |      |      |      |
|      |      |      |      | 2352 |      |      |      |      |      |      |
|      |      |      |      |      |      |      |      | 2460 |      |      |
| 2482 |      |      |      |      |      | 22   |      |      |      |      |
|      |      |      |      |      |      |      |      | 2718 |      |      |
|      |      |      |      |      |      |      | 2797 |      |      |      |
|      |      |      |      |      |      |      |      | 2884 |      |      |
|      |      |      |      |      |      |      |      | 2926 |      |      |

In order to analyze the possible effect of any such AFB₁ induced dG→T mutation, site-targeted mutagenesis study of the hhc<sup>M</sup> DNA was initiated using polynucleotides of 20 mers that carried a predicted dG→dT point-mutation, presumably the result of an AFB₁-epoxide mutagenesis. Thus far, only a few of the predicted dG→dT mutagenesis sites have been analyzed and these are summarized in Table 4. The recombinant construct carrying the hhc<sup>M</sup> sequence in the SV40 T antigen vector plus a neomycin resistance marker, rpN<sup>r</sup>pM-1 was used in this study since it offered the advantage of selecting the transfected cells by its resistance to Gentamicin sulfate (G418), an analog of neomycin. Using expression of hhc<sup>M</sup> specific mRA as a criterion, we analyzed by Northern dot-blot in a semi-quantitative assay of the mRNA, i.e. poly A enriched RNA, expressed in the G418 resistant NIH/3T3 cells after transfection with the mutagenized hhc<sup>M</sup> sequence. Focal transformation in these cells was monitored for 4 to 6 weeks.

Results from seven mutagenized clones, for which nucleotide sequence confirmation was available, suggested that, thus far, mutation leading to a structural protein alteration did not seem to potentiate the cell-transformation of hhc<sup>M</sup> (Table 4). Alternatively the introduced dG→T mutations which led to amino acid substitution, thus far, have not altered cell-transformation or expression of mRNA levels. These included mutation at 577 which caused an amino acid substitution of Gly→Val, and mutation at 1005 which resulted in no amino acid substitution because of the wobbling code.

Within the hhc<sup>M</sup> nucleotide sequence, there exists an apparent open reading frame, ORF, coding for a polypeptide of about 467 amino acids. This was in good agreement with a 55–57 kD protein and some smaller polypeptide including one 53 kD protein observed in cell-free protein synthesis using hhc<sup>M</sup>-specific mRNA in a rabbit reticulocyte lysate system. dG→T mutations at nucleotide 73 and 74 in the 5' terminus, which bears the consensus sequence for ribosomal RNA binding site just 5' ahead of the first methionine codon, blocked cell transformation although hhc<sup>M</sup> specific mRNA level showed no difference. This could be the result of blocking protein synthesis. Likewise, interpreted as a mutations at 492 and 550 also blocked cell-transformation since a stop codon (UGA) was introduced in each case to stop protein synthesis prematurely.

It was of interest to note that dG→T mutation at 626 generated a sequence resembling the enhancer sequence for RNA polymerase II, which was reported to function even within the coding sequence (footnote of Table 4). The level of mRNA level was increased by 1.5 fold and cell transformation seemed to be enhanced by a slight increase in the number of foci per μg of DNA. This observation suggested that one possible action by which AFB₁ induced mutation in hhc<sup>M</sup> which itself is a moderately transforming DNA sequence, led to increase in its transformation potential is through augmentation of hhc<sup>M</sup> expression. This is analogous to other observations which also indicated that an elevated expression of the cellular ras proto-onocgene driven by a murine LTR sequence, containing both promoter and enhancer sequence, also led to cell transformation in tissue culture cells predisposed to immortality.

TABLE 4

The Effect of dG→dT Mutation Induced by Site-Targetted Mutagenesis Within The hhc$^M$ DNA Sequence

| # on hhc$^M$ | Sequence | mRNA Synthesis# | Cell Transformation# |
|---|---|---|---|
| 73 | AGGA→A*TGA | + | −@1 |
| 74 | AGGA→AG*TG | + | −@1 |
| 492 | TGGG→TG*TG | + | −@2 |
| 550 | GGAG→G*TAG | + | −@2 |
| 577 | GGGC→G*TGC | ++ | + |
| 626 | GGGG→G*TGG | ++ | ++@3 |
| 1005 | TGCA→T*TCA | + | + |

@1Disruption of ribosomal RNA (16S) binding site: AGG*A.

@2Creation of a stop codon: UG*A.

@3Creation of an enhancer sequence: GGTGTGG*TAAAG (Watson et al., 1987; Dynan and Tjian, 1985; Schaffner et al. 1985) and hence increases expression.

Cell transformation was determined by transfection analysis as described in Methods and mRNA synthesis in transfected cells was determined by Northern dot-blot analysis with [$^{32}$P]3.1 kb hhc$^M$ DNA.

EXAMPLE III

Figure 5:
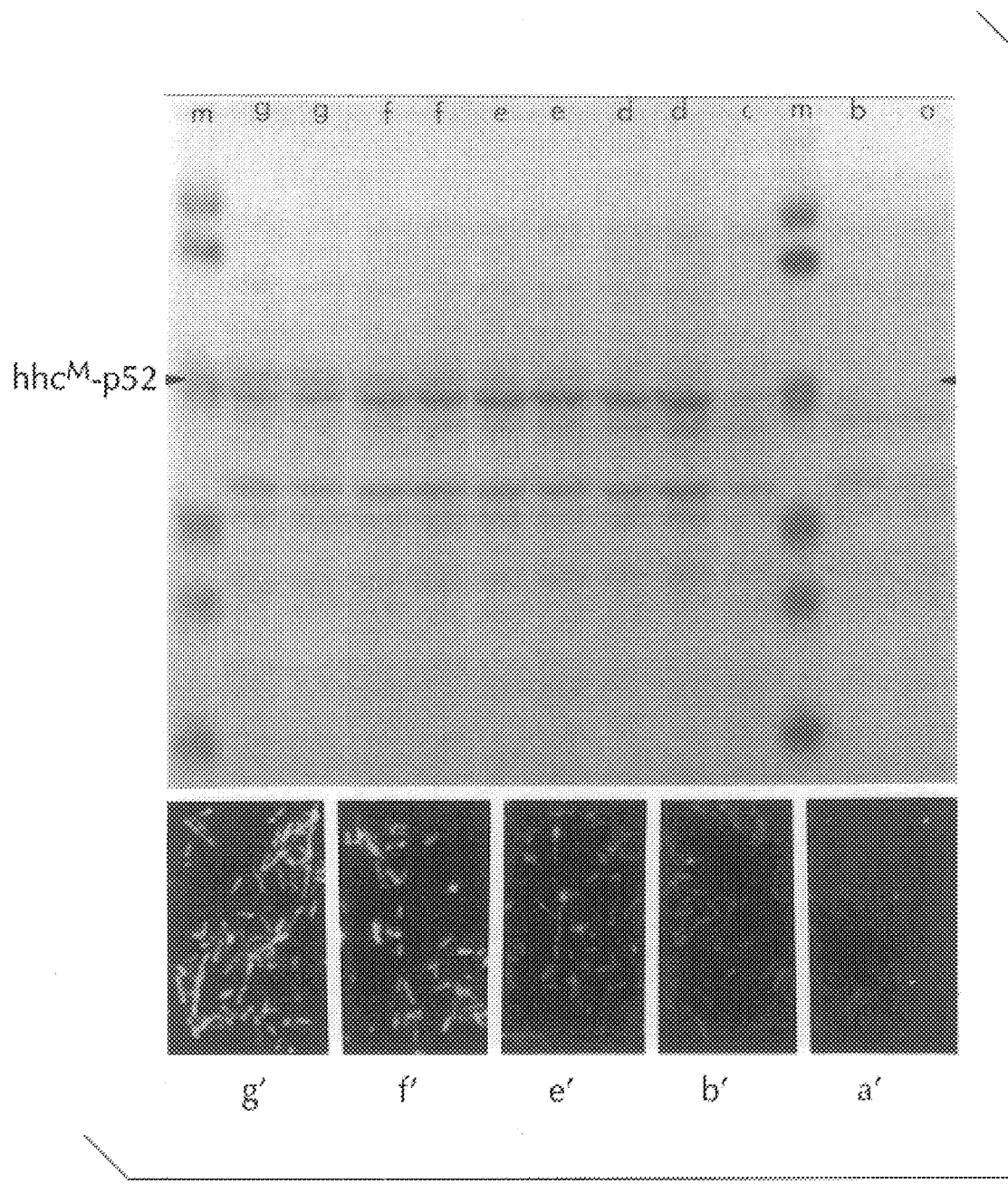
FIG. 5: Kinetic analysis of protein production in E. coli cells harboring pJZ102. Plasmid pJZ102 and control plasmid pJZ101 were cultured in E. coli cells until cell density reached a Klett reading of 80, at which point the inducer, IPTG (final concentration, 10$^{-3}$ mol), was added to activate transcription from the lac promoter for the production of the chimeric hhc$^M$-lac 52-kD protein. One ml samples of the cultures were removed at specified times, pelleted by centrifugation and lysed, and the proteins were denatured by boiling in Laemmli buffer. Equivalent aliquots of each sample were applied and analyzed by SDS-polyacrylamide gel electrophoresis as described in (Somerville et al., Structural and Organizational Aspects of Metabolic Regulation: UCLA Symposia on Molecular and Cellular Biology, New Series, Vol. 133, p. 181–197. New York: Alan R. Liss, Inc. 1990). The lanes represent: (a) pJZ102+ITPG at time zero; (b) pJZ102–ITPG at time zero, and 20 hours (c); pJZ102+ ITPG at 30 minutes (d), 4 hours (e), 7 hours (f), and 20 hours (g). Dark field microscopy of pJZ102 transformed E. coli cells+ITPG at 0 time (a'), 30 minutes (b'), 4 hours (e'), 7 hours (f'), and 20 hours (g'). Prestained molecular weight markers (m) in kD are 130 (faint band on top), 94, 75, 50, 39, 27, 17.

Hhc$^M$-D52 and anti-p52 and their use as screening and diagnostic reagents for human heratocellular carcinoma and related liver preneoplastic pathological conditions Hhc$^M$-p52 as a fusion protein was produced by a bacterial system described above at high levels (FIG. 5). This protein was used to generate a panel of both monoclonal and polyclonal antibodies against related human hepatoma proteins (see FIG. 6). Anti-p52, a polyvalent antibody against hhc$^M$-p52 was produced and shown to be highly specific against an African (Mahlavu) hepatoma and a Philadelphia hepatoma (FIG. 6).

Assays for the presence of hepatoma specific protein p52 in tumor samples entail diffusion and immunoprecipitation using the tumor sample extracts reacted with anti-p52, with or without radioactive or immunofluorescence labels. Further, anti-p52, labelled with either a radioactive compound or with a chromophore, is useful in RIPA or color-change assays, respectively, for testing for the presence of hepatoma related proteins shed by the patient in sera and urine samples. Fluorescence imagery analysis using anti-p52 conjugated to a fluorescence compound or another suitable compound for systemic perfusion, provide the ability to localize in situ preneoplastic or neoplastic lesions by scanning. Localization of lesions permits laser removal with surgical precision, and/or other treatment.

Figure 7:
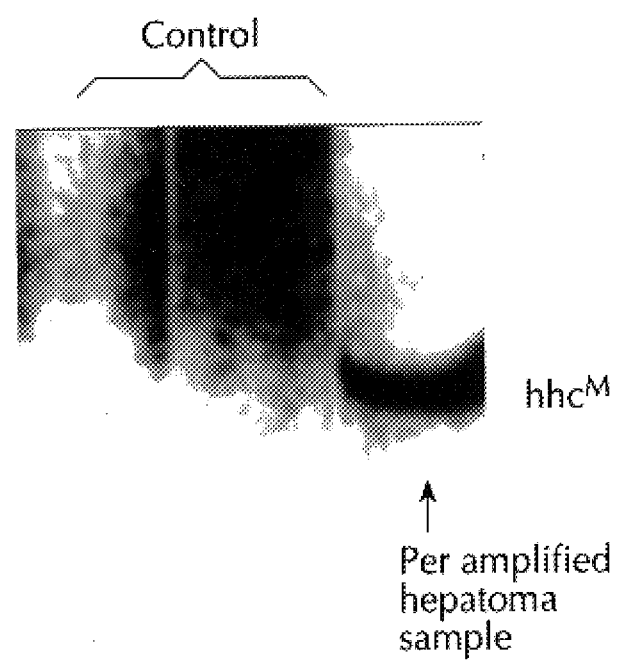
FIG. 7: DNA-DNA hybridization against $^{32}$P-hhc$^M$ DNA.

Hhc$^M$-p52 nucleotide sequence, labelled appropriately, can be applied to diagnose hepatomas in biopsy samples. Hhc$^M$-related nucleic acid sequences can be detected in needle biopsy samples of patients suspected of carrying preneoplastic nodules or liver cancer. This is accomplished by the using the polymerase chain reaction to amplify "hhc$^M$-like" sequences using fragments of the hhc$^M$-p52 sequence as primers, and then detecting the presence of such hhc$^M$-like sequences in the biopsy sample with labelled hhc$^M$-p52 as a probe in a DNA-DNA hybridization reaction. Such an example is shown in FIG. 7.

The entire contents of all references cited herein are hereby incorporated by reference.

The present invention has been described in some detail for purposes of clarity and understanding. One skilled in the art will appreciate from a reading of this disclosure that various changes in form and detail can be made without departing from the true scope of the invention.

What is claimed is:

1. An isolated and purified protein having the amino acid sequence set forth as follows Met Leu Pro Phe Thr Cys Gly Arg Asn Ala Asn Glu Asn Ser Pro Arg Asp Val Asp Val Gly Val Ala Pro Ala Ala Glu Gly Asn Val Gln His Val Glu Gly Ser Thr Ala Lys Ala Gly Leu Ser Ser Arg Ser Gly Gly Gly Gly Ser Leu Ser His Leu Phe Cys Glu Cys Ser Ser Lys Pro Cys Leu Lys His Val Glu Lys Leu Ser Glu Leu Pro Pro Gly His MET Gln MET Asp Thr Leu Ile Ile Lys Leu Ser Gly Arg Leu Arg Asn Lys Thr Lys MET Glu Val Pro Pro Asn Gln Trp Lys Phe Phe Pro Phe Ser Phe Leu Trp His Ser Leu Ala Leu Thr Gln Gly Ser Pro His Ser Arg Ser Arg His Gln Gly Thr Gly Gly Glu Leu Trp Gly Thr Leu Gln Ala Tyr Ser Val Asn Gly Leu Ala Ala Ala Thr Gly Ala Thr MET Glu Pro Ala Gly Thr His Asn Thr Glu Gly Arg Asp Leu Ala Ser Asn Gln Ile Ser Cys Asp Ser Arg Glu Gly Gly Val Lys Ala Thr Gly Leu Phe Leu Ser Thr Ser Ser His Val MET Thr Pro Glu Gly Arg Arg Gly Arg Lys Cys Glu His Arg Asp Ile MET Ser Arg Ser Leu Leu Thr Arg Cys Pro Lys Glu Glu Ser Gln Val Thr Thr Gln His Gln Arg Asn Cys Arg Val MET Arg Asn Phe Gly Lys Gln Ser Ile Val Leu Ser Val Lys Pro Leu Ala His Ser Arg Ala Gly His Ala Trp MET Val Thr Leu Asp Gly Ile Asp Tyr Glu Glu Pro Gly Gln Gly Ile Tyr Leu His Arg Asp Val Arg Val Thr Cys Ile Pro Lys His His Glu Ala Leu Lys Thr Glu Leu MET Trp Lys Pro Gln Pro Leu Gln Val Ala Leu His Leu Gln His Lys Pro Asn His Ile Asn Cys Cys Lys Thr Lys Leu Gln His Ser Pro Tyr His Leu Asn Lys Thr Gln Ser Leu Thr Thr Phe Lys Thr Pro Arg Thr Gln Ser Lys Ile Thr Ser Thr Lys Asn Gln Glu Asn Leu Asn Glu Gln Gly Lys Trp Gln Ser Val Ala Ala Ser Ala Glu MET Thr MET Trp Val Gly Ile Ile Asn Ile Phe Lys Val Ile Ile Ile Ser Ile Leu Gly Gln Val MET Ala Asn Thr Leu Glu Ile Asn Gly Lys Ile Arg Arg Leu Arg Glu Lys Val Glu Cys Thr Lys Asn Asp Gln Val Gly Ile Ala Pro Leu Glu Thr Asn His Gln Asp Lys Ala Val Ser Gly Trp Ala Asn Arg Arg MET Glu MET Lys Arg Glu Arg Val Val MET Ala Val Val Gln Phe Glu Gln His Lys Arg His or a naturally occurring allelic variation of said sequence.

2. The isolated and purified protein according to claim 1 wherein said protein has the amino acid sequence set forth as follows Met Leu Pro Phe Thr Cys Gly Arg Asn Ala Asn Glu Asn Ser Pro Arg Asp Val Asp Val Gly Val Ala Pro Ala Ala Glu Gly Asn Val Gln His Val Glu Gly Ser Thr Ala Lys Ala Gly Leu Ser Ser Arg Ser Gly Gly Gly Gly Ser Leu Ser His Leu Phe Cys Glu Cys Ser Ser Lys Pro Cys Leu Lys His Val Glu Lys Leu Ser Glu Leu Pro Pro Gly His MET Gln MET Asp Thr Leu Ile Ile Lys Leu Ser Gly Arg Leu Arg Asn Lys Thr Lys MET Glu Val Pro Pro Asn Gln Trp Lys Phe Phe Pro Phe Ser Phe Leu Trp His Ser Leu Ala Leu Thr Gln Gly Ser Pro His Ser Arg Ser Arg His Gln Gly Thr Gly Gly Glu Leu Trp Gly Thr Leu Gln Ala Tyr Ser Val Asn Gly Leu Ala Ala Ala Thr Gly Ala Thr MET Glu Pro Ala Gly Thr His Asn Thr Glu Gly Arg Asp Leu Ala Ser Asn Gln Ile Ser Cys Asp Ser Arg Glu Gly Gly Val Lys Ala Thr Gly Leu Phe Leu Ser Thr Ser Ser His Val MET Thr Pro Glu Gly Arg Arg Gly Arg Lys Cys Glu His Arg Asp Ile MET Ser Arg Ser Leu Leu Thr Arg Cys Pro Lys Glu Glu Ser Gln Val Thr Thr Gln His Gln Arg Asn Cys Arg Val MET Arg Asn Phe Gly Lys Gln Ser Ile Val Leu Ser Val Lys Pro Leu Ala His Ser Arg Ala Gly His Ala Trp MET Val Thr Leu Asp Gly Ile Asp Tyr Glu Glu Pro Gly Gln Gly Ile Tyr Leu His Arg Asp Val Arg Val Thr Cys Ile Pro Lys His His Glu Ala Leu Lys Thr Glu Leu MET Trp Lys Pro Gln Pro Leu Gln Val Ala Leu His Leu Gln His Lys Pro Asn His Ile Asn Cys Cys Lys Thr Lys Leu Gln His Ser Pro Tyr His Leu Asn Lys Thr Gln Ser Leu Thr Thr Phe Lys
Thr Pro Arg Thr Gln Ser Lys Ile Thr Ser Thr Lys Asn Gln
Glu Asn Leu Asn Glu Gln Gly Lys Trp Gln Ser Val Ala Ala
Ser Ala Glu MET Thr MET Trp Val Gly Ile Ile Asn Ile Phe
Lys Val Ile Ile Ile Ser Ile Leu Gly Gln Val MET Ala Asn Thr
Leu Glu Ile Asn Gly Lys Ile Arg Arg Leu Arg Glu Lys Val
Glu Cys Thr Lys Asn Asp Gln Val Gly Ile Ala Pro Leu Glu
Thr Asn His Gln Asp Lys Ala Val Ser Gly Trp Ala Asn Arg
Arg MET Glu MET Lys Arg Glu Arg Val Val MET Ala Val
Val Gln Phe Glu Gln His Lys Arg His.

3. A process of producing the protein according to claim 1 comprising:

a) culturing a host cell transformed with a recombinant DNA molecule, said molecule comprising:
  i) a vector, and
  ii) a DNA fragment coding for said protein, under conditions such that said DNA fragment is expressed and said protein is thereby produced; and b) isolating said protein.

* * * * *

UNITED STATES PATENT AND TRADEMARK OFFICE
CERTIFICATE OF CORRECTION

Page 1 of 2

PATENT NO.   :   5,811,262

DATED        :   September 22, 1998

INVENTOR(S)  :   Stringner S. YANG

It is certified that error(s) appear in the above-identified patent and that said Letters Patent is hereby Corrected as shown below:

In column 2, line 27, replace "FIG. 1" with -- FIGS. 1A-1C --.

In column 2, lines 40-41, replace "FIG. 1" with -- FIGS. 1A-1C --.

In column 3, line 26, replace "FIG. 1" with -- FIGS. 1A-1C --.

In column 3, line 33, replace "FIG. 1" with -- FIGS. 1A-1C --.

Figure 6A:
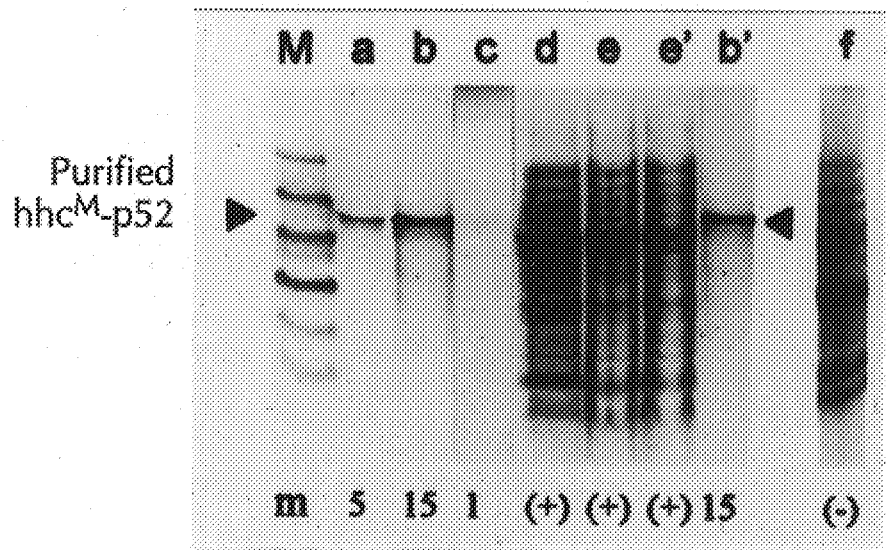
FIG. 6: (A) Purified hhc$^M$ fusion protein p52 produced in bacteria and (B) specificity of a polyclonal anti-p52 IgG. A, SDS-polyacrylamide gel electrophoresis of bacterially expressed p52. All conditions for the bacterial expression of chimeric hhc$^M$-lac fusion proteins were as described in FIG. 5. Lanes d, e, and e' represent total cell extracts of pJZ102-bearing E. coli cells (in varying amounts) induced by IPTG and lane f represents the total cell extracts of a negative control pJZ101-bearing E. coli cells. Lanes a (5 μl), b (15 μl) and c (1 μl) depict different amounts of gel purified p52 that was used to immunize rabbits. Lane m depicts prestained molecular markers in kD of 75, 57, 50, 39, 27, 17.
Figure 6B:
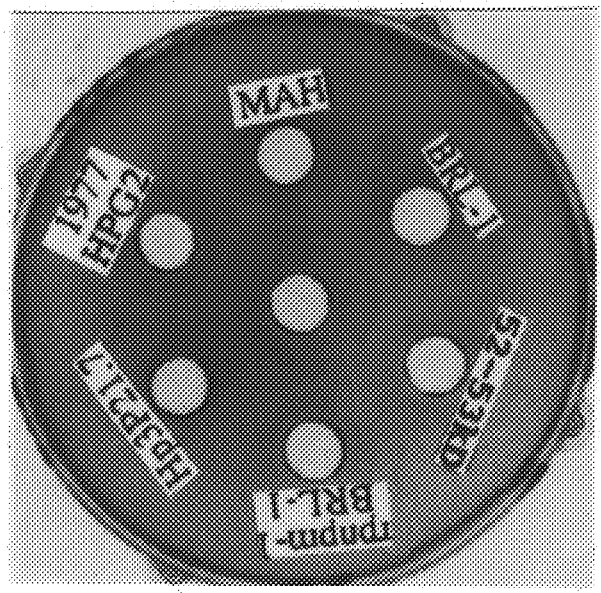

In column 4, line 7, replace "FIG. 6" with -- FIGS. 6A-6B --.

In column 4, line 7, replace "(A)" with -- FIG. 6(A) --.

In column 4, line 8, replace "(B)" with -- FIG. 6(B) --.

In column 4, line 15, insert -- and b' -- after "lanes a (5µl), b".

In column 4, line 19, replace "(B)" with -- FIG. 6(B) --.

In column 4, line 53, replace "FIG. 1" with -- FIGS. 1A-1C --.

In column 4, line 56, replace "FIG. 1" with -- FIGS. 1A-1C --.

In column 4, line 57, replace "FIG. 1" with -- FIGS. 1A-1C --.

In column 4, line 60, replace "FIG. 1" with -- FIGS. 1A-1C --.

In column 5, line 8, replace "FIG. 1" with -- FIGS. 1A-1C --.

In column 5, line 9, replace "FIG. 1" with -- FIGS. 1A-1C --.

In column 5, line 14, replace "FIG. 1" with -- FIGS. 1A-1C --.

In column 5, line 23, replace "FIG. 1" with -- FIGS. 1A-1C --.

In column 15, line 30, replace "Hhc$^M$-D52" with -- hhc$^M$-p52 --.

In column 15, line 33, replace "Hhc$^M$-p52" with -- hhc$^M$-p52 --.

In column 15, line 40, replace "(FIG. 6)" with -- (FIGS. 6A-6B) --.

UNITED STATES PATENT AND TRADEMARK OFFICE
CERTIFICATE OF CORRECTION

PATENT NO. : 5,811,262
DATED : September 22, 1998
INVENTOR(S) : Stringner S. YANG It is certified that error appears in the above-identified patent and that said Letters Patent is hereby corrected as shown below:

In column 15, line 55, replace "Hhc$^M$-p52" with -- hhc$^M$-p52 --.

In column 15, line 57, replace "Hhc$^M$-p52" with -- hhc$^M$-p52 --.

Signed and Sealed this

Eighteenth Day of April, 2000

Attest:

Q. TODD DICKINSON

*Attesting Officer*   *Director of Patents and Trademarks*